(12) United States Patent
Oliverius et al.

(10) Patent No.: US 12,096,977 B2
(45) Date of Patent: *Sep. 24, 2024

(54) ELECTROPHYSIOLOGY CATHETER WITH MODULAR ELECTRODE STRUCTURE

(71) Applicant: St. Jude Medical, Cardiology Division, Inc., St. Paul, MN (US)

(72) Inventors: Andrew R. Oliverius, Eagan, MN (US); Timothy S. Marass, Minneapolis, MN (US); Therese C. Gilbert, St. Paul, MN (US); Nicholas Strom, Minneapolis, MN (US); Gregory K. Olson, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 698 days.

This patent is subject to a terminal disclaimer.

(21) Appl. No.: 17/317,420

(22) Filed: May 11, 2021

(65) Prior Publication Data
US 2021/0267676 A1    Sep. 2, 2021

Related U.S. Application Data

(63) Continuation of application No. 16/173,750, filed on Oct. 29, 2018, now Pat. No. 11,033,327.
(Continued)

(51) Int. Cl.
  *A61B 18/14*    (2006.01)
  *A61B 5/287*    (2021.01)
  (Continued)

(52) U.S. Cl.
  CPC .......... *A61B 18/1492* (2013.01); *A61B 5/287* (2021.01); *A61M 25/0067* (2013.01);
  (Continued)

(58) Field of Classification Search
  CPC ...... A61B 18/1492; A61B 2018/00577; A61B 5/0422; A61B 2018/00351; A61B 5/6852;
  (Continued)

(56) References Cited

U.S. PATENT DOCUMENTS

| | | |
|---|---|---|
| 4,890,623 A | 1/1990 | Cook |
| 5,199,433 A | 4/1993 | Metzger |

(Continued)

*Primary Examiner* — Joseph A Stoklosa
*Assistant Examiner* — Brian M Antiskay
(74) *Attorney, Agent, or Firm* — Wiley Rein LLP

(57) ABSTRACT

A modular multi-electrode structure for use with an electrophysiology device includes a plurality of interconnected, non-conductive, tubular substrates. Each non-conductive, tubular substrate includes an outer surface and a conductor disposed on the outer surface, as well as at least one signal conductor extending along a length of the interconnected plurality of non-conductive tubular substrates. The conductor disposed on the outer surface of each non-conductive tubular substrate is in electrical communication with the at least one signal conductor. In some embodiments, the plurality of non-conductive tubular substrates includes a plurality of non-conductive polymeric substrates. In alternative (Continued)

embodiments, the plurality of non-conductive tubular substrates includes a plurality of non-conductive, unitary molded cylinders.

18 Claims, 13 Drawing Sheets

Related U.S. Application Data

(60) Provisional application No. 62/578,566, filed on Oct. 30, 2017.

(51) Int. Cl.
*A61M 25/00* (2006.01)
*A61B 17/00* (2006.01)
*A61B 18/00* (2006.01)
*A61N 1/05* (2006.01)

(52) U.S. Cl.
CPC ........... *A61B 2017/00053* (2013.01); *A61B 2018/00172* (2013.01); *A61B 2018/00178* (2013.01); *A61B 2018/00839* (2013.01); *A61B 2018/1467* (2013.01); *A61B 2018/1495* (2013.01); *A61N 1/05* (2013.01)

(58) Field of Classification Search
CPC .......... A61B 2018/1475; A61B 5/0538; A61B 5/6858; A61M 25/0147; A61M 2210/125; A61N 1/05
USPC ........ 600/372–375, 377, 380–381, 393, 435, 600/466–467, 481, 508–509; 606/20–52; 607/115, 122–124
See application file for complete search history.

(56) References Cited

U.S. PATENT DOCUMENTS

| | | | |
|---|---|---|---|
| 5,499,981 | A | 3/1996 | Kordis |
| 5,667,615 | A | 9/1997 | Maurer |
| 7,669,309 | B2 | 3/2010 | Johnson |
| 9,955,917 | B2 | 5/2018 | Bitzer |
| 2002/0013537 | A1 | 1/2002 | Rock |
| 2005/0203599 | A1 | 9/2005 | Garabedian |
| 2006/0206023 | A1 | 9/2006 | Bernhart |
| 2008/0172051 | A1 | 7/2008 | Masuda |
| 2009/0240249 | A1 | 9/2009 | Chan |
| 2010/0094279 | A1 | 4/2010 | Kauphusman |
| 2014/0378803 | A1 | 12/2014 | Geistert |
| 2015/0273184 | A1 | 10/2015 | Scott |
| 2016/0184008 | A1 | 6/2016 | Papaioannou |
| 2017/0189107 | A1 | 7/2017 | Wulfman |

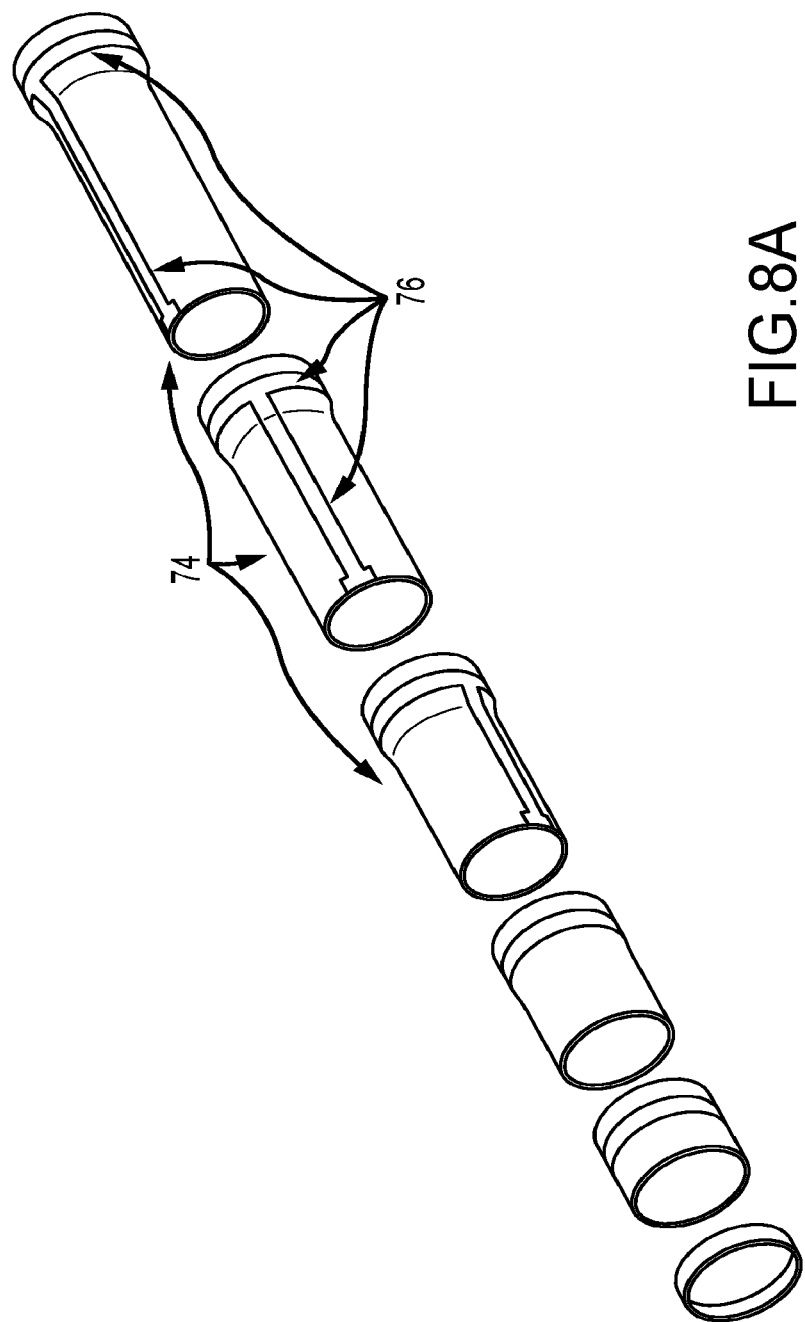

ELECTROPHYSIOLOGY CATHETER WITH MODULAR ELECTRODE STRUCTURE

CROSS-REFERENCE TO RELATED APPLICATIONS

This application is a continuation of U.S. patent application Ser. No. 16/173,750, filed 29 Oct. 2018 ("the '750 application"), now pending, which claims the benefit of U.S. provisional application No. 62/578,566, filed 30 Oct. 2017 ("the '566 provisional"). Both the '750 application and the '566 provisional are hereby incorporated by reference as though fully set forth herein.

BACKGROUND

The instant disclosure relates to medical devices. In particular, the instant disclosure relates to multi-electrode electrophysiology catheters that are usable, inter alia, for tissue ablation and electrophysiological mapping.

Catheters are used in a variety of diagnostic and therapeutic procedures, for example to diagnose and/or treat conditions such as atrial and ventricular arrhythmias. For example, a catheter carrying one or more electrodes can be deployed and manipulated through a patient's vasculature and, once located at the intended site, radiofrequency ("RF") energy can be delivered through the electrodes to ablate tissue. Multi-electrode catheters can also be used to generate cardiac geometries/model surfaces and/or electrophysiology maps.

Various extant multi-electrode catheters can have certain specific advantages and shortcomings. For example, ablation catheters often have improved steerability relative to catheters used for electrophysiology mapping, making them well-suited for accessing hard-to-reach areas. Yet, because they have a relatively small number of widely-spaced electrodes (that is, they are relatively low density), they are not as well-suited to gathering electrophysiology data.

Electrophysiology mapping catheters, on the other hand, typically have a higher density of electrodes (e.g., 10-20 electrodes with various inter-electrode spacing), making them well-suited to gathering electrophysiology data, but less maneuverable and less well-suited to the delivery of therapy (e.g., ablation).

Because of these tradeoffs, extant devices generally are not used to perform multiple functions, potentially requiring multiple devices to be inserted into and removed from a patient's body during a single procedure. For example, during an electrophysiology procedure, a high density multi-electrode catheter may be used to generate an electrophysiology map. Once the map is created, the high density mapping catheter can be removed and an RF ablation catheter inserted in its place.

Yet, many practitioners would find it advantageous, for example, to conduct additional electrophysiology assessments (e.g., isochronal activation maps, geometry creation, lesion/scar quality assessments, and the like), both during and after the ablation (e.g., to judge the efficacy of the ablation), and it would be efficient to do so with the same catheter that was used to deliver the ablation in the first instance. It would also be advantageous to use more highly-maneuverable ablation catheters to map the electrophysiological activity in hard-to-reach areas, but without compromising the speed with which electrophysiology maps can be generated when using high density multi-electrode catheters.

BRIEF SUMMARY

Disclosed herein is a modular multi-electrode structure for use with an electrophysiology device, including: a plurality of non-conductive cylinders; and a plurality of electrodes, wherein the plurality of non-conductive cylinders are connected to form a stack, and wherein the plurality of electrodes are positioned between adjacent non-conductive cylinders of the stack.

In aspects of the disclosure, adjacent non-conductive cylinders are interconnected in the stack via snap elements on the adjacent non-conductive cylinders. For example, the snap elements on the adjacent non-conductive cylinders can include: at least one barb on a first non-conductive cylinder of the adjacent non-conductive cylinders; and a corresponding at least one catch on a second non-conducive cylinder of the adjacent non-conductive cylinders.

In other aspects of the disclosure, adjacent non-conductive cylinders are interconnected in the stack via adhesive.

In embodiments, each non-conductive cylinder includes a shoulder configured to receive an electrode of the plurality of electrodes, thereby to position the plurality of electrodes between adjacent non-conductive cylinders of the stack.

In additional embodiments, each non-conductive cylinder includes a longitudinally-extending slot in a wall thereof, wherein the longitudinally-extending slot is configured to receive a signal conductor. The modular multi-electrode structure can also include a signal conductor, such as a printed circuit board, extending longitudinally along the stack through the longitudinally-extending slots of the plurality of non-conductive cylinders.

The modular multi-electrode structure can include a non-conductive shaft interconnect cylinder, wherein the non-conductive shaft interconnect cylinder is connected to a proximal end of the stack. For example, the non-conductive shaft interconnect cylinder can include a reflow retention structure configured to be secured to a catheter shaft.

It is contemplated that the plurality of electrodes can include a plurality of ring electrodes. It is also contemplated that each electrode of the plurality of electrodes can include an integrated signal conductor terminal. Likewise, it is contemplated that each non-conductive cylinder can include a unitary molded component.

Also disclosed herein is a modular multi-electrode structure for use with an electrophysiology device, including: a plurality of cylindrical segments, each cylindrical segment including: a non-conductive tubular substrate; and a conductive trace on an outer surface of the non-conductive tubular substrate, wherein the plurality of cylindrical segments are nested such that only a portion of the conductive trace of each cylindrical segment is exposed. According to aspects of the disclosure, the conductive traces of adjacently-nested cylindrical segments can be electrically isolated from each other.

In embodiments of the disclosure, at least a portion of the conductive trace extends along a length of the outer surface of the non-conductive tubular substrate. The conductive trace can also extend around at least a portion of the outer surface of the non-conductive tubular substrate perpendicular to the at least a portion of the conductive trace that extends along the length of the outer surface of the non-conductive tubular substrate.

The instant disclosure also provides a modular multi-electrode structure for use with an electrophysiology device, including: a plurality of interconnected, non-conductive, tubular substrates, each non-conductive, tubular substrate having an outer surface and a conductor disposed on the outer surface; and at least one signal conductor extending along a length of the interconnected plurality of non-conductive tubular substrates, wherein the conductor disposed on the outer surface of each non-conductive tubular substrate is in electrical communication with the at least one signal conductor.

The plurality of non-conductive tubular substrates can include a plurality of non-conductive polymeric substrates. Alternatively, the plurality of non-conductive tubular substrates can include a plurality of non-conductive, unitary molded cylinders.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 8A is an exploded isometric view of a multi-electrode structure according to another embodiment of the instant disclosure.

DETAILED DESCRIPTION

Figure 1:
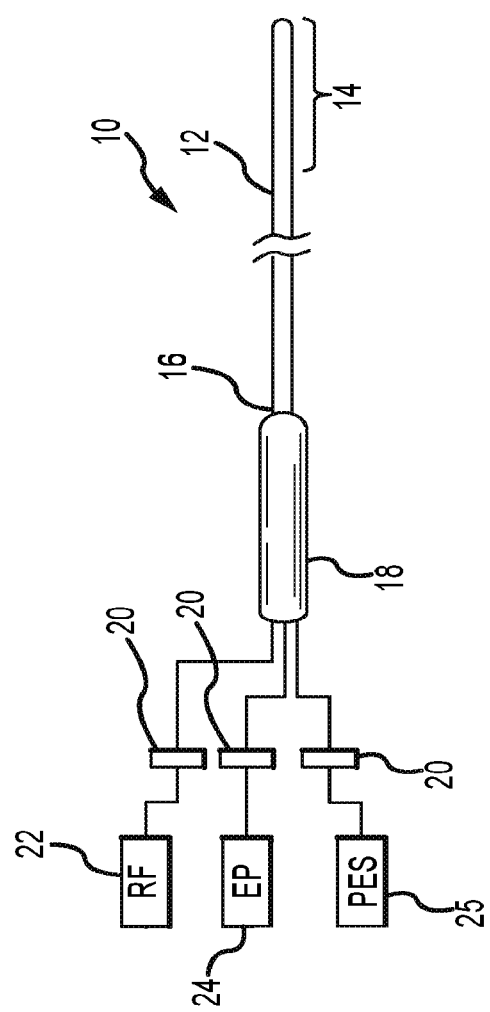
FIG. 1 schematically depicts an electrophysiology catheter and associated systems.

For purposes of illustration, the present teachings will be described in connection with a high density multi-electrode mapping and ablation catheter 10, such as illustrated in FIG. 1. Catheter 10 generally includes an elongate catheter body 12 having a distal region 14 and a proximal end 16. A handle 18 is shown coupled to proximal end 16. FIG. 1 also shows connectors 20. Connectors 20 are configured to be connected to a source of ablation energy (schematically illustrated as RF source 22, which can be, for example, the Ampere™ RF ablation generator of Abbott Laboratories), an electrophysiology mapping device (schematically illustrated as 24, which can be, for example, the EnSite Precision™ cardiac mapping system, also of Abbott Laboratories), and a programmable electrical stimulator (schematically illustrated as 25, which can be, for example the EP-4™ cardiac stimulator, also of Abbott Laboratories). Although FIG. 1 depicts three separate connectors 20, it is within the scope of the instant disclosure to have a combined connector 20 that is configured for connection to two or more of RF source 22, electrophysiology mapping device 24, and programmable electrical stimulator 25.

Various additional aspects of the construction of catheter 10 will be familiar to those of ordinary skill in the art. For example, the person of ordinary skill in the art will recognize that catheter 10 can be made steerable, for example by incorporating an actuator into handle 18 that is coupled to one or more steering wires that extend through elongate catheter body 12 and that terminate in one or more pull rings within distal region 14. Likewise, the ordinarily skilled artisan will appreciate that catheter 10 can be an irrigated catheter, such that it can also be coupled to a suitable supply of irrigation fluid and/or an irrigation pump. As a further example, those of ordinary skill in the art will appreciate that catheter 10 can be equipped with force feedback capabilities.

Insofar as such features are not necessary to an understanding of the instant disclosure, they are neither illustrated in the drawings nor explained in detail herein. By way of example only, however, catheter 10 can incorporate various aspects and features the following catheters, all from Abbott Laboratories: the EnSite™ Array™ catheter; the FlexAbility™ ablation catheter; the Safire™ BLU™ ablation catheter; the Therapy™ Cool Path™ irrigated ablation catheter; the Livewire™ TC ablation catheter; and the TactiCath™ Quartz irrigated ablation catheter.

Figure 2:
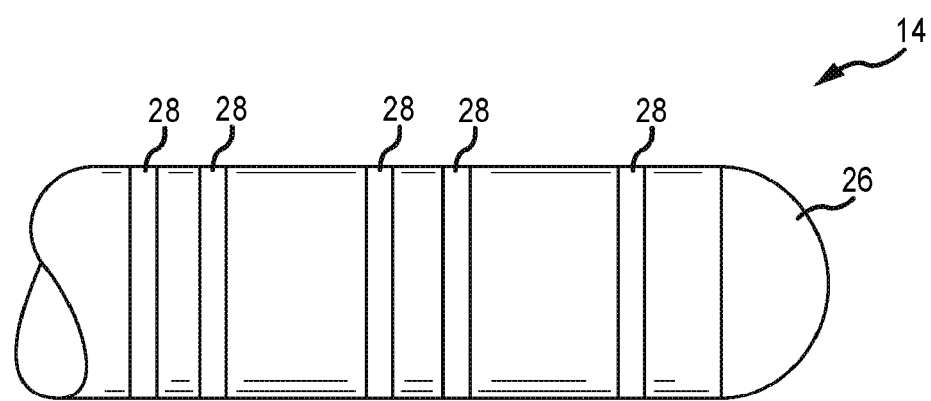
FIG. 2 is a close-up view of the distal region of the catheter shown in FIG. 1.

FIG. 2 is a close-up of distal region 14 of catheter 10. Distal region 14 of catheter 10 includes a tip electrode 26 positioned at its distal end and a plurality of additional electrodes 28 proximal of tip electrode 26. The most proximal of electrodes 28 will, in certain embodiments, be no more than about 10 mm from the distal tip of distal region 14, but it is contemplated that it can be more proximally located (e.g., in some embodiments, up to about 24 mm from the distal tip of distal region 14, or, in other embodiments, up to about 31 mm from the distal tip of distal region 14).

FIG. 2 depicts five ring electrodes 28. In embodiments, each electrode is between about 0.25 mm and about 0.5 mm wide, with an inter-electrode spacing of about 1 mm or less.

From the disclosure herein, the person of ordinary skill in the art will understand and appreciate that, by varying the size (e.g., width) and spacing of electrodes 28, different diagnostic and/or therapeutic objectives and/or outcomes can be achieved. For example, the ordinarily skilled artisan will appreciate that, as electrodes 28 become smaller and closer together, the electrograms collected thereby will become sharper and more localized evidencing better depiction of local, near-field depolarization of the cardiac tissue in contact with the electrodes. Thus, it should be understood that distal region 14 can include any number of such electrodes 28 (e.g., 9 electrodes 28 for a decapolar catheter 10) and that the inter-electrode spacing can vary along the length of distal region 14.

Electrodes 28 can be of various physical configurations. These include, by way of example only, ring electrodes, segmented ring electrodes, partial ring electrodes, and spot electrodes. Various configurations of electrodes 28 (as well as electrode 26) are disclosed in International Publication No. WO 2016/182876, which is hereby incorporated by reference as though fully set forth herein.

Disclosed herein are modular multi-electrode structures that can be employed to good advantage in connection with electrophysiology catheters such as catheter 10 described above.

Figure 3A:
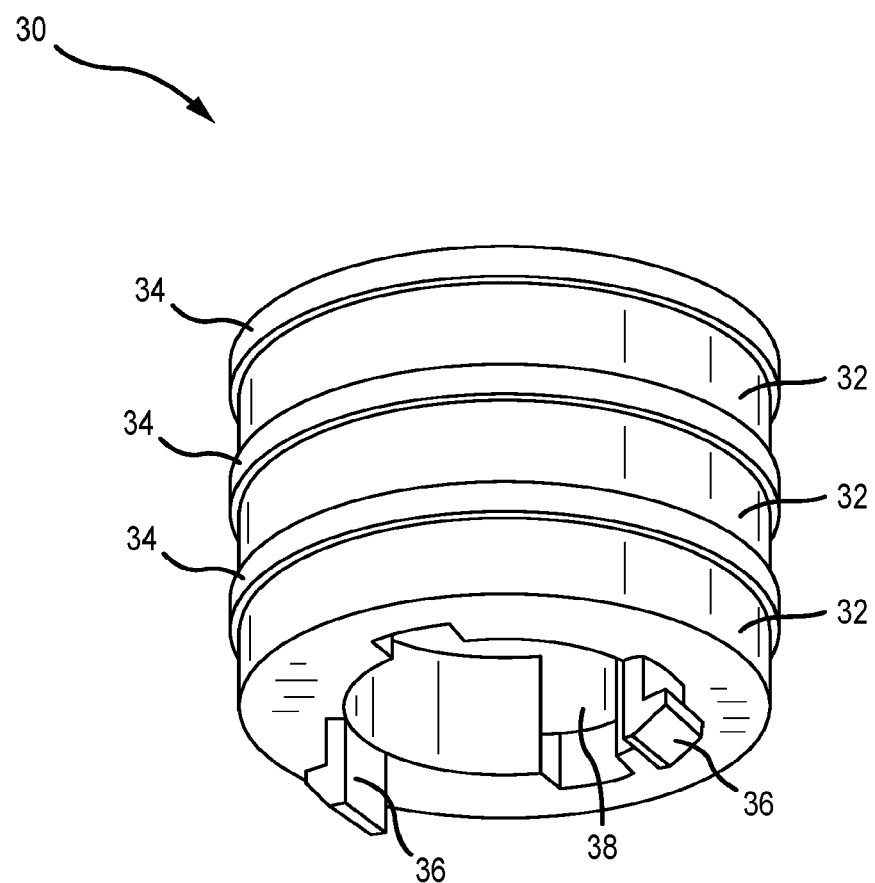
FIG. 3A depicts a multi-electrode structure according to an embodiment of the instant disclosure.

A first embodiment of a modular multi-electrode structure 30 according to the teachings will be described with reference to FIGS. 3A and 3B. As shown in FIG. 3A, modular multi-electrode structure 30 includes a plurality of non-conductive cylinders 32 and a plurality of electrodes 34. The plurality of non-conductive cylinders 32 are interconnected to form a stack, with the plurality of electrodes 34 positioned between adjacent ones of the interconnected non-conductive cylinders 32 as shown.

Figure 3B:
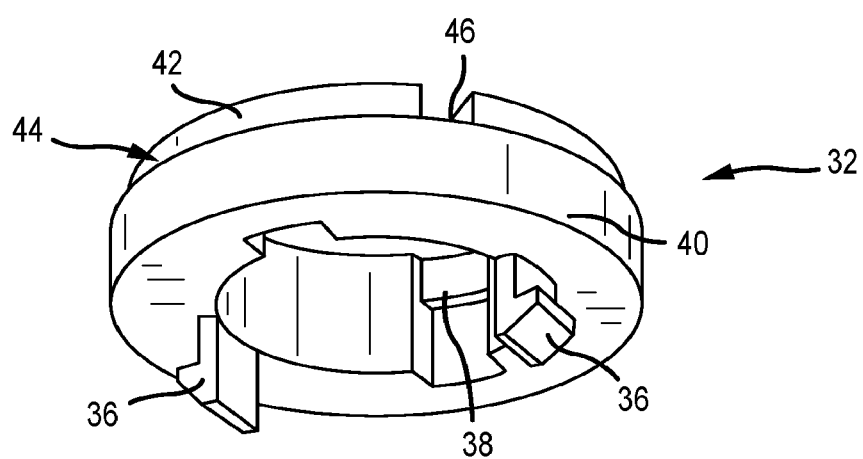
FIG. 3B illustrates details of the non-conductive cylinders used in the construction of the multi-electrode structure of FIG. 3A.

FIG. 3B illustrates certain details of a non-conductive cylinder 32. For example, FIG. 3B illustrates barbs 36 and corresponding catches 38 that cooperate as snap elements to interconnect adjacent non-conductive cylinders 32 to form multi-electrode structure 30. As shown in FIG. 3B, non-conductive cylinder 32 includes two diametrically-opposed barbs 36 and two diametrically opposed catches 38 approximately halfway therebetween. Other numbers and configurations of barbs 36 and/or catches 38 are regarded as within the scope of the instant disclosure.

FIG. 3B also depicts to good advantage that non-conductive cylinder 32 contains a large diameter portion 40 and a small diameter portion 42, with the transition between large diameter portion 40 and small diameter portion 42 defining a shoulder 44. Electrode 34 fits around small diameter portion 42 (e.g., the outer diameter of small diameter portion 42 approximates the inner diameter of electrode 34) and rests on shoulder 44. Advantageously, this simplifies the assembly of multi-electrode structure 30 by reducing or eliminating the need for mechanical electrode swaging during assembly of catheter 10.

Another advantage is that non-conductive cylinder 32 reduces the variability in inter-electrode spacing and concentricity during assembly of catheter 10. The width (oriented along the vertical axis in FIG. 3B) of large diameter portion 40 dictates the inter-electrode spacing within multi-electrode structure 30. As discussed above, the inter-electrode spacing can be fixed (e.g., the width of large diameter portion 40 of each non-conductive cylinder 32 can be the same) or varying (e.g., the width of large diameter portion 40 can differ from non-conductive cylinder 32 to non-conductive cylinder 32).

FIG. 3B also illustrates a slot 46 that extends longitudinally through the wall of non-conductive cylinder 32. As discussed in greater detail below, slot 46 is configured to receive a signal conductor (e.g., a conductor to connect electrodes 34 to RF source 22, electrophysiology mapping device 24, and/or programmable electrical stimulator 25) in a manner that advantageously reduces or eliminates the need to feed electrode signal wires through multi-electrode structure 30 using a stylet.

Figure 4A:
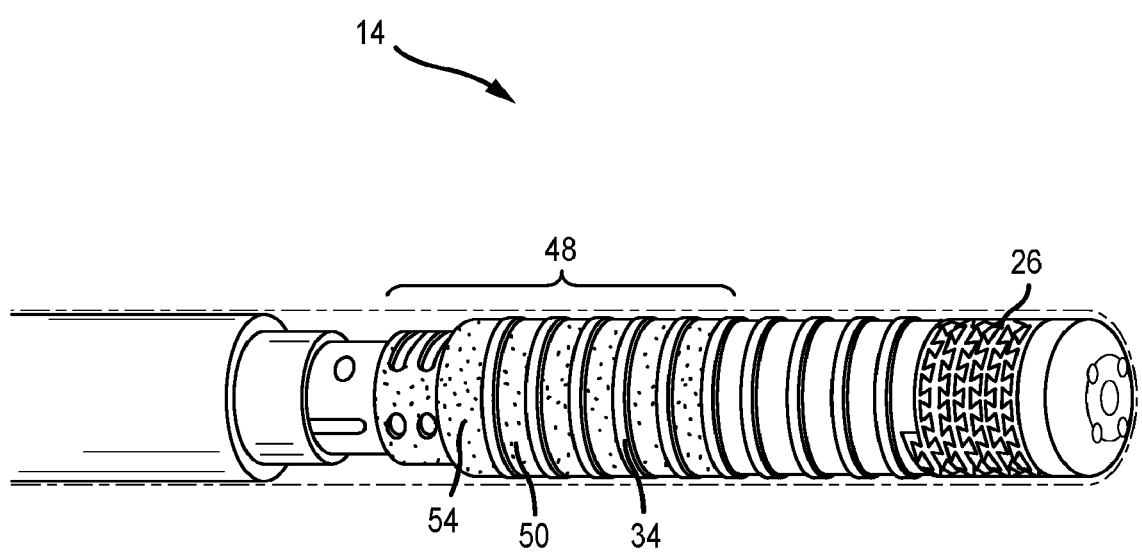
FIG. 4A depicts a multi-electrode structure according to another embodiment of the instant disclosure, shown in the context of a high density multi-electrode electrophysiology catheter.

FIG. 4A depicts a multi-electrode structure 48 according to another embodiment of the instant teachings, shown in context with distal region 14 of catheter 10. As shown in FIG. 4A, multi-electrode structure 48 includes a plurality of non-conductive cylinders 50, interconnected to form a stack, and a plurality of electrodes 34 positioned between adjacent ones of the interconnected non-conductive cylinders 50 as shown.

Figure 4B:
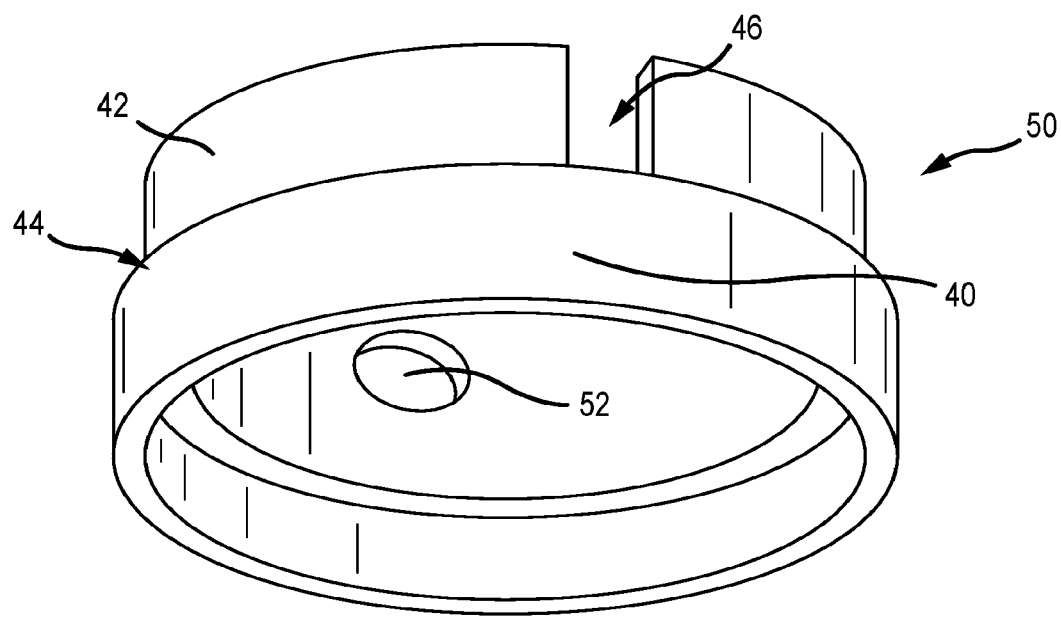
FIG. 4B illustrates details of some of the non-conductive cylinders used in the construction of the multi-electrode structure of FIG. 4A.

FIG. 4B illustrates certain details of a non-conductive cylinder 50. Those details of non-conductive cylinder 50 that are in common with non-conductive cylinder 32 (e.g., shoulder 44, slot 46, and so forth) need not be discussed further. Those of ordinary skill in the art should note that non-conductive cylinder 50 does not include snap elements (e.g., barbs 36 and corresponding catches 38), which allows for an increased inner diameter of non-conductive cylinder 50. Instead, non-conductive cylinder 50 includes one or more through holes 52 to facilitate adhesively interconnecting adjacent non-conductive cylinders 50 in multi-electrode structure 48.

Figure 4C:
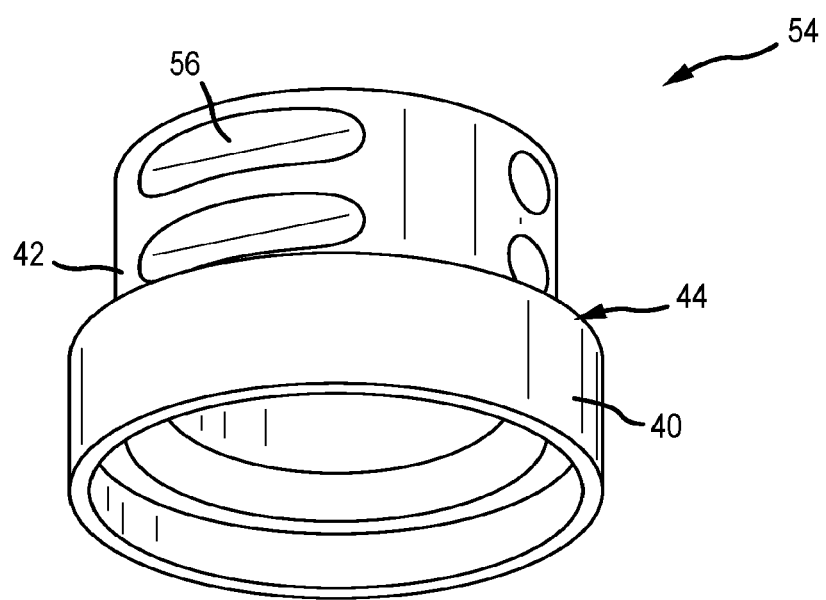
FIG. 4C illustrates details of other non-conductive cylinders that can be used in the construction of the multi-electrode structure of FIG. 4A.

FIG. 4C illustrates a non-conductive shaft interconnect cylinder 54, which can be the most proximal component of multi-electrode structure 48. Shaft interconnect cylinder 54 includes a reflow retention structure 56, which is configured to allow multi-electrode structure 48 to be secured to elongate catheter body 12 during reflow processing.

Figure 5:
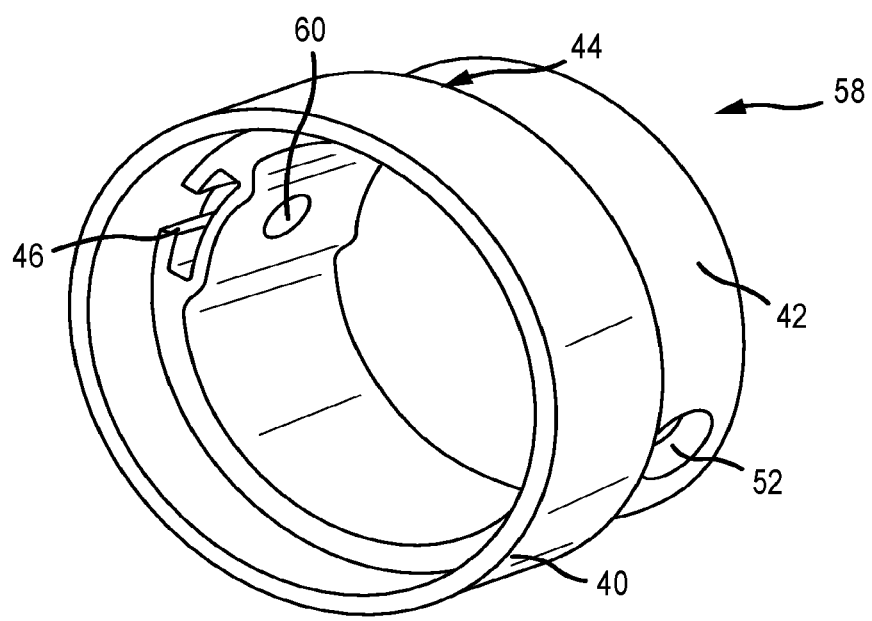
FIG. 5 depicts a non-conductive cylinder that can be used in the construction of a multi-electrode structure according to aspects of the instant disclosure.

FIG. 5 depicts a non-conductive cylinder 58 according to another embodiment of the instant teachings. As shown in FIG. 5, slot 46 includes a via 60. Via 60 provides a pathway to electrically interconnect electrodes 34 to the signal conductor passing through slot 46.

Figure 6A:
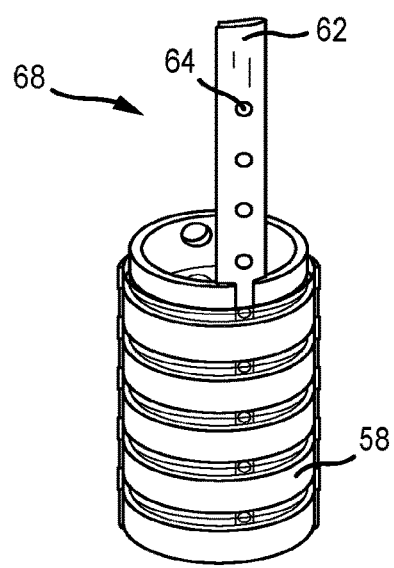
FIGS. 6A and 6B illustrate a multi-electrode structure and a signal conductor.
Figure 6B:
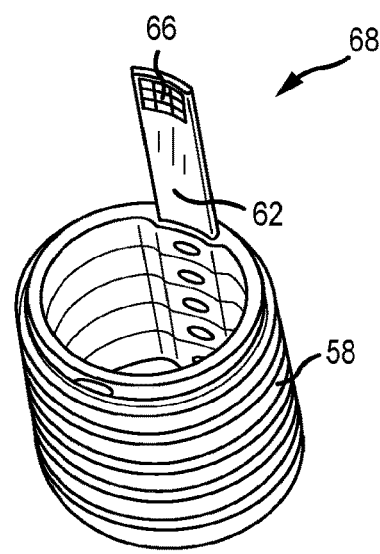

For example, as shown in FIGS. 6A and 6B, a printed circuit board 62, including a plurality of electrode termination contacts 64 and a plurality of wire termination contacts 66, can extend through slot 46 within a multi-electrode structure 68 (for clarity, electrodes 34 are not shown in FIGS. 6A and 6B).

Figure 7A:
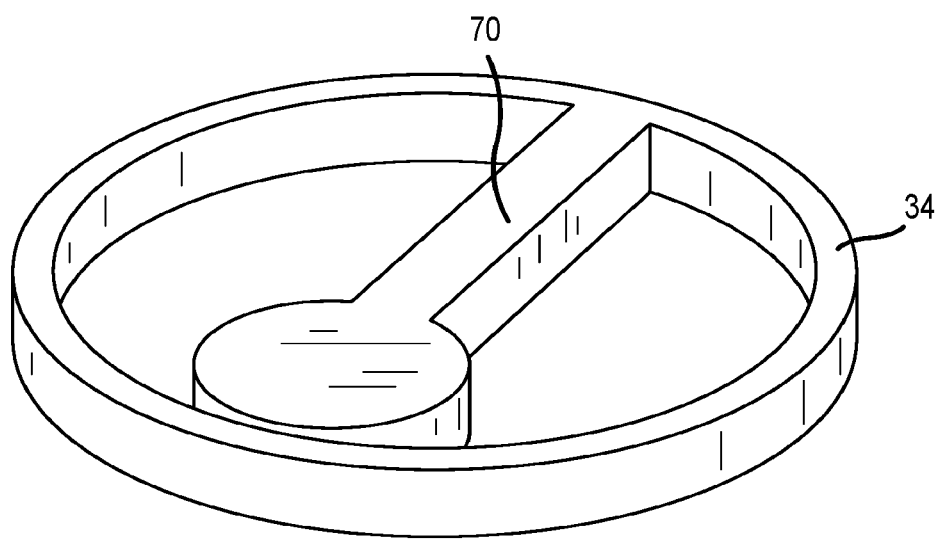
FIGS. 7A and 7B illustrate an electrode with an integrated, flexible terminal.
Figure 7B:
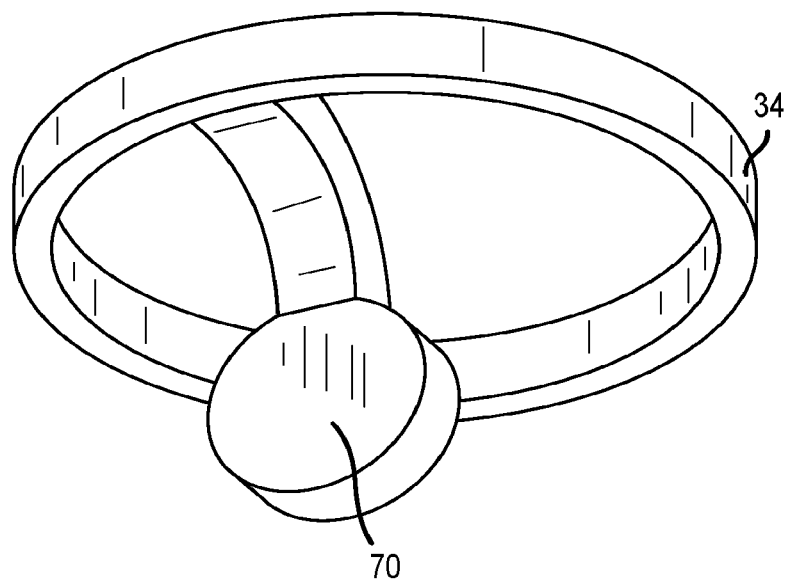

As shown in FIG. 7A, electrode 34 can include an integrated, flexible signal conductor terminal 70. By bending terminal 70 out of the plane of electrode 34 as shown in FIG. 7B, it can be passed through via 60 and into electrical contact with a corresponding electrode termination contact 64. Advantageously, this simplifies the connection between the signal conductor and the electrode, reducing or eliminating the need to laser-weld or otherwise affix the signal conductor to the electrode during assembly of catheter 10.

Any of the foregoing non-conductive cylinders (e.g., 32, 50, 54, 58) can be formed as a unitary molded component, for example by micromolding. This offers several advantages, including reduced manufacturing cost, reduced manufacturing time, reduced manufacturing variability, and reduced manufacturing complexity. Additional manufacturing efficiencies can be gained, for example, by manufacturing electrodes 34 via a stamping process.

Figure 8B:
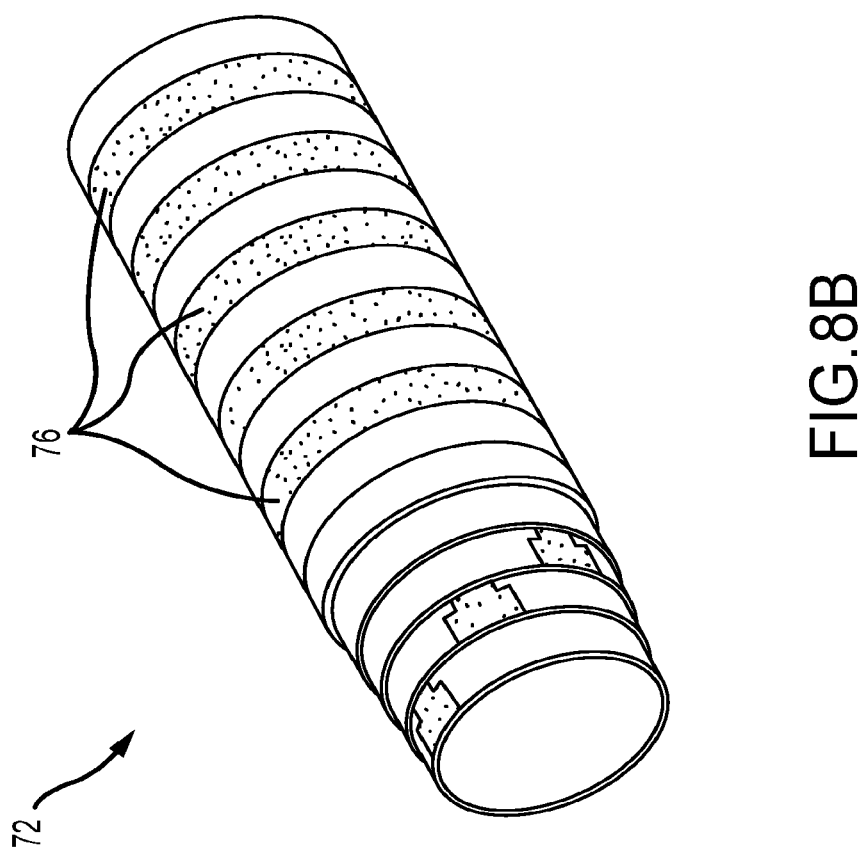
FIG. 8B is an isometric view of an assembled multi-electrode structure corresponding to the exploded view of FIG. 8A.

Yet another embodiment of a multi-electrode structure 72 according to the teachings herein is depicted in FIGS. 8A and 8B. As best illustrated in FIG. 8B, multi-electrode structure 72 includes a plurality of cylindrical segments, each including a non-conductive tubular substrate 74 and a conductive trace 76 on an outer surface thereof. As shown in FIG. 8A, the plurality of cylindrical segments are nested such that only a portion of each conductive trace 76 is exposed. For example, the portion of conductive trace 76 that extends around (e.g., circumferentially) at least a portion of the outer surface non-conductive tubular substrate 74 can remain exposed to function as a ring electrode. Similarly, the portion of conductive trace 76 that extends along the length of the outer surface of non-conductive tubular substrate 74 can function as a signal conductor, connecting the electrode portion of conductive trace 76 to RF source 22, electrophysiology mapping device 24, and/or programmable electrical stimulator 25.

In some embodiments, conductive trace 76 is only on the outer surface of non-conductive tubular substrate 74, such that the conductive traces 76 of adjacently-nested cylindrical segments remain electrically isolated from each other. It is also contemplated, however, to provide one or more vias through a non-conductive tubular substrate 74 to enable electrical interconnection between the conductive traces 76 of adjacently-nested cylindrical segments.

Although several embodiments of this invention have been described above with a certain degree of particularity, those skilled in the art could make numerous alterations to the disclosed embodiments without departing from the spirit or scope of this invention.

For example, the multi-electrode structures described herein can be applied to good advantage in connection with mapping catheters (e.g., the Advisor™ FL circular mapping catheter, Sensor Enabled™ of Abbott Laboratories) as well as combination mapping and ablation catheters (e.g., the FlexAbility™ ablation catheter, Sensor Enabled™ of Abbott Laboratories).

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A modular multi-electrode structure for use with an electrophysiology device, comprising:
   a plurality of non-conductive cylinders; and
   a plurality of electrodes,
   wherein the plurality of non-conductive cylinders are directly connected to and in contact with each other to form a stack,
   wherein the plurality of electrodes are positioned between adjacent non-conductive cylinders of the stack, and
   wherein the stack has a fixed length.

2. The modular multi-electrode structure according to claim 1, wherein the adjacent non-conductive cylinders are interconnected in the stack via snap elements on the adjacent non-conductive cylinders.

3. The modular multi-electrode structure according to claim 2, wherein the snap elements on the adjacent non-conductive cylinders comprise:
   at least one barb on a first non-conductive cylinder of the adjacent non-conductive cylinders; and
   a corresponding at least one catch on a second non-conductive cylinder of the adjacent non-conductive cylinders.

4. The modular multi-electrode structure according to claim 1, wherein the adjacent non-conductive cylinders are interconnected in the stack via adhesive.

5. The modular multi-electrode structure according to claim 1, wherein each non-conductive cylinder comprises a shoulder configured to receive an electrode of the plurality of electrodes, thereby to position the plurality of electrodes between the adjacent non-conductive cylinders of the stack.

6. The modular multi-electrode structure according to claim 1, wherein each non-conductive cylinder of the plurality of non-conductive cylinders comprises a longitudinally-extending slot in a wall thereof, wherein the longitudinally-extending slot is configured to receive a signal conductor.

7. The modular multi-electrode structure according to claim 6, further comprising a signal conductor extending longitudinally along the stack through the longitudinally-extending slots of the plurality of non-conductive cylinders.

8. The modular multi-electrode structure according to claim 7, wherein the signal conductor comprises a printed circuit board.

9. The modular multi-electrode structure according to claim 1, further comprising a non-conductive shaft interconnect cylinder, wherein the non-conductive shaft interconnect cylinder is connected to a proximal end of the stack.

10. The modular multi-electrode structure according to claim 9, wherein the non-conductive shaft interconnect cylinder comprises a reflow retention structure configured to be secured to a catheter shaft.

11. The modular multi-electrode structure according to claim 1, wherein the plurality of electrodes comprises a plurality of ring electrodes.

12. The modular multi-electrode structure according to claim 1, wherein each electrode of the plurality of electrodes comprises an integrated signal conductor terminal.

13. The modular multi-electrode structure according to claim 1, wherein each non-conductive cylinder of the plurality of non-conductive cylinders comprises a unitary molded component.

14. A modular multi-electrode structure for use with an electrophysiology device, comprising:
   a plurality of non-conductive cylinders, wherein each non-conductive cylinder of the plurality of non-conductive cylinders is in contact with and attached to at least one additional non-conductive cylinder of the plurality of non-conductive cylinders, wherein a distance between adjacent non-conductive cylinders of the plurality of non-conductive cylinders is fixed, thereby forming a stack having a fixed length and defining an outer circumferential wall; and
   a plurality of electrodes disposed around the outer circumferential wall of the stack.

15. The modular multi-electrode structure according to claim 14, wherein the adjacent non-conductive cylinders of the plurality of non-conductive cylinders are attached to each other via snap elements on the adjacent non-conductive cylinders.

16. The modular multi-electrode structure according to claim 15, wherein the snap elements on the adjacent non-conductive cylinders comprise:
   at least one barb on a first non-conductive cylinder of the adjacent non-conductive cylinders; and
   a corresponding at least one catch on a second non-conductive cylinder of the adjacent non-conductive cylinders.

17. The modular multi-electrode structure according to claim 14, wherein the adjacent non-conductive cylinders of the plurality of non-conductive cylinders are attached to each other via adhesive.

18. The modular multi-electrode structure according to claim 14, wherein each non-conductive cylinder comprises a shoulder configured to receive an electrode of the plurality of electrodes.

* * * * *